United States Patent
Martinez et al.

(10) Patent No.: US 8,841,251 B2
(45) Date of Patent: Sep. 23, 2014

(54) METHOD FOR MAKING A HOMOGENOUS VACCINE COMPOSITION COMPRISING A CONJUGATE OF EGF AND 64K FOR THE TREATMENT OF TUMORS

(75) Inventors: Gryssell Rodriguez Martinez, Havana (CU); Lisel Vina Rodriguez, Havana (CU); Loany Calvo Gonzalez, Havana (CU); Ariadna Cuevas Fiallo, Havana (CU); Ernesto Chico Veliz, Havana (CU); Agustin Bienvenido Lage Davila, Havana (CU); Tania Crombet Ramos, Havana (CU); Arama Albisa Novo, Havana (CU); Gisela Maria Gonzalez Marinello, Havana (CU)

(73) Assignee: Centro de Immunologia Molecular (CIM), Havana (CU)

( * ) Notice: Subject to any disclaimer, the term of this patent is extended or adjusted under 35 U.S.C. 154(b) by 346 days.

(21) Appl. No.: 13/346,831

(22) Filed: Jan. 10, 2012

(65) Prior Publication Data

US 2013/0039940 A1   Feb. 14, 2013

Related U.S. Application Data

(62) Division of application No. 12/664,545, filed as application No. PCT/CU2008/000005 on Jun. 26, 2008.

(30) Foreign Application Priority Data

Jun. 29, 2007 (CU) .................................. 154-2007

(51) Int. Cl.
*A61K 38/18* (2006.01)
*A61P 35/00* (2006.01)
*C07K 14/485* (2006.01)
*C07K 19/00* (2006.01)
*C07K 1/34* (2006.01)
*A61K 39/00* (2006.01)

(52) U.S. Cl.
CPC ..... *A61K 39/0011* (2013.01); *A61K 2039/6031* (2013.01)
USPC ........... 514/9.6; 514/19.3; 530/350; 530/402; 530/414

(58) Field of Classification Search
None
See application file for complete search history.

(56) References Cited

U.S. PATENT DOCUMENTS 5,894,018 A * 4/1999 Davila et al. ............. 424/195.11
2006/0013800 A1 * 1/2006 Le Buanec et al. .......... 424/85.1

OTHER PUBLICATIONS

Gonzalez et al (Jan./Feb. 2007. Human Vaccines. 3(1): 8-13).*

* cited by examiner

*Primary Examiner* — Zachary Howard
(74) *Attorney, Agent, or Firm* — Lackenbach Siegel, LLP

(57) ABSTRACT

A vaccine composition for therapeutic use thereof on cancer patients includes a chemical conjugate of human recombining Epidermic Growth Factor (hrEGF) and a combining protein P64k for performing a conjugation reaction which produces said chemical conjugate in a controlled and reproducible manner. The preferred conjugate surprisingly increases the immunogenic activity causing significant increases in the anti-EGF antibody titers in humans, and provides a vaccine preparation with more than one type of effective dose presentation which enables the immunization dose per patient to be increased, but without involving an increase in immunization frequency and/or the number of immunization sites.

7 Claims, 4 Drawing Sheets

METHOD FOR MAKING A HOMOGENOUS VACCINE COMPOSITION COMPRISING A CONJUGATE OF EGF AND 64K FOR THE TREATMENT OF TUMORS

PRIOR RELATED APPLICATIONS

This application is a divisional patent application of U.S. patent application Ser. No. 12/664,545, Filed Apr. 19, 2010, which claims priority to and is a U.S. 371 Patent Application of PCT Patent Application, Serial No. PCT/CU2008/000005, filed Jun. 26, 2008, which claims priority to Cuban Patent Application, Serial No. CU 154-2007, filed Jun. 29, 2007 and incorporates the above-referenced applications in their entireties by reference thereto.

FIELD OF THE INVENTION

The present invention relates to biotechnology, particularly with the human health. In an embodiment, the present invention describes protective and/or therapeutic cancer vaccines, principally vaccine compositions to elicit a significant increase of the immune response against the Epidermal Growth Factor (EGF), whose oncological relevance has been broadly demonstrated, mainly for the growth of tumors of epithelial origin.

The EGF receptor (EGFR) system, including the ligands, is a molecular complex which specifically regulates the cellular growth and its effect on the uncontrolled growth of epithelial tumors.

In the tumorigenic process, the deregulation of paracrine and autocrine processes for activation of the EGRF, involve the over-expression of the growth factors as well as the increased synthesis and/or mutation of the receptors.

The EGF is a 53 amino acids polypeptide, with an apparent molecular weight of 6045 Da. This peptide was isolated and purified for the first time by Cohen S., J. Biol. Chem. 20 (1962) 237, 1.555).

The EGF is a member of the EGFR ligands family; this family comprises structural and functionally related proteins. Others members of this family are: Transforming Growth Factor (TGF), anmphiregulin (AR), criptol (CR1), heparine binding growth factor, betaceluline and ephireguline. On the other hand the family of the poxvirus includes proteins related with the EGF; among them the most characterized is the vaccinia virus growth factor (VGF).

All these molecules are able to bind the EGFR with the consequent receptor activation, so they are known as EGFR ligands and play a role in the normal and tumor cell growth.

The EGFR is a 170 kDa glycoprotein; the gene has already been cloned and sequenced. The intra-cellular domain of this receptor is associated with the tyrosine kynase activity of molecules that shows a structural homology with those proteins coded by the v-erb-B oncogen, and they are involved with the malignant transformation process (HELDIN C. H. (1984), CELL 37, 9-20.).

The experimental evidences of the last years about the relation between the EGFR and its ligands system with cancer, makes it a very attractive target for cancer immunotherapy.

Previous results have demonstrated the efficacy for cancer of the active immunotherapy with the EGF based vaccine. In fact, preclinical and clinical evidences have been obtained about the immunogenicity and lack of toxicity caused by vaccination with the hrEGF linked to a carrier protein (González and cols. (1996), Vaccine Research 5(4), 233-243.)

EP 0 657 175 describe a vaccine composition that comprises autologous EGF coupled to carrier protein which inhibit the growth of EGF depending tumors by an autoimmune effect.

The vaccine composition described in EP 0 657 175, is conjugated vaccines comprising the EGF coupled to a carrier protein (the P64K protein, the cholera toxin B chain, the titanic toxoid protein and/or monoclonal antibodies) and as a consequence is obtained an heterogeneous and low reproducible mixture of conjugated species.

The novel vaccine composition described in the present invention comprises the autologous EGF as active principle, and is characterized for having a homogeneous chemical composition, with a defined purity, eliciting higher immunogenicity, a substantially increased clinical activity and with fewer immunizations for getting a therapeutical effect.

The lower autologous antigen content in the vaccine composition of the present invention surprisingly doesn't induce lower EGF antibody titers in humans by the contrary, it rather induce significant increase of the anti-EGF antibody titers. The lower amount of EGF contents and its derivatives in the vaccine composition was obtained by developing of a purification method based on membrane filtration, which is also an object of the present invention.

Furthermore, the present invention provides a homogeneous and reproducible vaccine composition with a higher clinical effect and lower immunizations, meaning a great advantage in cancer therapy and for the patient, in comparison with vaccine compositions previously described.

The vaccine composition of the present invention could also comprise appropriate adjuvants such as aluminum hydroxide or MONTANIDE, a mixture of a mineral oil and a surfactant.

In another embodiment, the present invention relates to a sanitary procedure for the manufacture of said vaccine composition, appropriate for its use in humans by parenteral route.

The procedure comprises a suitable method for the covalent conjugation of the hrEGF to the carrier protein P64K, and the purification of this conjugated by using ultra filtration membranes in a range of 50-100 kDa, to remove the biologically inactive species conjugated (without immunogenic activity), as well as other chemical impurities.

DETAILED DESCRIPTION OF THE INVENTION

The present invention discloses a novel vaccine composition based on the autologous EGF having said vaccine composition a homogeneous chemical composition with defined purity, and which is able to elicit potentate immunogenicity and a substantially increased clinical activity. Additionally, with the vaccine composition of the present invention are able higher therapeutic doses without increasing the number of injections when the therapeutic dose must be increased, because by the procedure to obtain the vaccine composition of the present invention it is possible to increase the concentration of the conjugated species hrEGF-rP64K, which is known as potency.

Surprisingly, the inventors found that when decreasing the content of the autologous antigen by a novel purification procedure the vaccine composition of the present invention is able to elicit a significant increase of the immune response against the autologous EGF in comparison with heterogeneous EGF-based vaccines previously reported.

The vaccine composition obtained from the decrease of the content of the autologous antigen through the membrane ultrafiltration purification methodology has a homogeneous composition where the immunologically active species (conjugated species hrEGF-rP64K) shows molecular weight superior to 60 kDa. This vaccine composition shows a molecular exclusion chromatographic profile characterized because the species carrying the biological activity represents more than the 90% of the total chromatogram area, corresponding to the total vaccine composition, as it is shown in FIG. 4.

Mass Spectrometry analysis of the present vaccine composition has revealed its structural features. The peptide maps of two different lots show a high homology between lots in the position s as well as in the ratio (FIG. 5). This high homology between lots confirms the accuracy of the parameters of the chemical conjugation as well as the purification procedures, both described by the present invention. Mass Spectrometry analysis further revealed the sequence of the major peptides derived from the vaccine composition of the present invention. (Table 3).

In the present vaccine composition the conjugation ratio between the EGF and P64K proteins is 1:2, which means 2 molecules of EGF per P64K molecule.

Methodology for Obtaining the Vaccine Composition
Purification Procedure for Decreasing the Content of Autologous EGF Starting from experimental observations that evidenced that a decrease on the hrEGF content in the vaccine composition increase its immunological action, is developed a method for decrease the content in hrEGF in the heterogeneous mixture of conjugates; enriching the vaccine composition in conjugated species of high molecular weight (immunologically active species) and free of glutaraldehyde.

The purification procedure using ultrafiltration membranes in a range among 50-100 kDa developed and described in the present invention, consists of two stages: In the initial stage successive changes of tampon solution are performed (diafiltration) to remove glutaraldehyde and to eliminate the excess of autologous protein, either free or forming conjugated hrEGF-hrEGF of different sizes. During this stage, between 10 and 15 changes of the tampon solution are carried out.

The second stage is the concentration of the purified chemical conjugated, in which more than 90% of its composition corresponds to immunogenic species hrEGF-rP64K.

During the concentration stage the initial volume of the chemical conjugated is reduced until reaching a final protein concentration (conjugated species hrEGF-rP64K) in a range among 1-12 mg/mL. This versatility in the range of concentrations of the active principle (total milligrams of conjugated hrEGFrP64K for milliliters) for this vaccine composition is a great advantage for cancer therapy. This allows increasing the treatment dose without implying for the patient an increment in the frequency of immunization and/or an increase in the number of immunization sites.

With the purpose of monitoring the quality of the purification of the chemical conjugated it was evaluated the pH and the conductivity of the one retained and of the permeate. It was also carried out the determination of protein concentration by the method described by Lowry D. H. and col. J. Biol Chem 191: 495-498, 1951 and the percent of homogeneity were determined from the analysis of the gel filtration chromatography (HPLC-FG).

The singularity of this methodology assures that the obtained vaccine composition has a homogeneous composition and defined purity, characterized by the major presence of the immunologically active species: conjugated hrEGF-rP64K.

Surprisingly, the removal of the excess of autologous protein (hrEGF) free or polymeric doesn't cause the reduction, but rather it allows to increase significantly the concentration of anti-EGF antibodies (at 1/1000 dilution), to 10 times more this obtained when immunizing mice with polymers of hrEGF and with free hrEGF. The reduction of the content of autologous protein in the vaccine composition causes in patient increments of at least 2 times the maximum titer of anti EGF antibodies. This increment of the antibody titers is even observed in those patients that receive half of per immunization (2.4 mg) in comparison with patients that receive dose of 4.8 mg per dose of the vaccine composition described in EP 0657 175. These results indicate that the vaccine composition, described in the present invention has bigger immunological activity per milligram of immunologically active protein, as compared with other vaccine compositions.

Obtaining a Chemical Conjugated Between the Recombinant Protein P64K (rP64K) and the Human Recombinant Epidermal Growth Factor (hrEGF)

Starting from the evaluation and optimization of the conditions for the chemical conjugation reaction between the proteins hrEGF and rP64K a conjugation method is developed that requires of a high molar proportion of the autologous protein, 10 moles of hrEGF for each rP64K mol, to guarantee high conjugation efficiency among both. The necessary excess of autologous protein during the chemical conjugation, to guarantee its efficiency, is eliminated subsequently through the purification method of membrane ultrafiltration as previously described, that allows obtaining a vaccine composition with high homogeneity. The procedure described in the present invention to guarantee an appropriate chemical conjugation among both proteins consists of a single step and begins mixing the hrEGF protein previously concentrated (>6 mg/mL) and the protein rP64K (≥1 mg/mL) in the conjugation reactor. To this protein mixture is added the PBS/$MgCl_2$ solution (pH 6.8-7.2) and the conjugation solution of glutaraldehyde 0.5%. The mixture is maintained in constant stirring for 2 hours at temperature 22° C.±2° C. The final protein concentration in the reaction mixture for the hrEGF is 0.82 mg/mL and for the protein rP64K it is 0.89 mg/mL. The total protein concentration during the conjugation reaction is of 2 mg/mL and the final concentration of the glutaraldehyde in the reaction mixture is of 0.05%.

The vaccine composition according to the present invention can be employed together with appropriated adjuvants, such as aluminum hydroxide or MONTANIDE, a mixture of a mineral oil and a surfactant.

In another aspect, the present invention involves a sanitary procedure for obtaining of a vaccine composition, to be administered by parenteral route, procedure that minimizes the opportunities of microbial contamination of the vaccine composition during the conjugation allowing to carry out the purification methodology of the chemical conjugated in few hours and facilitating the increment of the volume of the vaccine composition to be obtained, among other advantages. The following examples illustrate more in detail the present invention.

The Example 1 describes the molecular characterization of the vaccine composition described in the present invention. The molecular characterization includes: the chromatographic identification by HPLC-FG of the conjugated species formed during the conjugation reaction, the determination of the conjugation ratio between the proteins hrEGF and rP64K and the definition of the peptides map that characterizes to this novel vaccine composition.

The Example 2 describes the bio-assays in mouse carried out to evaluate the immunogenicity of the novel vaccine composition described in the present invention.

The Example 3 describes the effectiveness in the clinical use of the present vaccine composition in the treatment of lung tumors of epithelial origin.

The Example 4 describe obtaining the vaccine compositions adjusted a at different potency (total milligrams of conjugated hrEGF-rP64K/vial), using the same conjugation methodology and purification as described in the present invention.

The Example 5 shows the removal of the glutaraldehyde used in the conjugation reaction by means of the purification methodology of the chemical conjugated through a 50 kDa ultrafiltration membrane.

EXAMPLES

Example 1

Molecular Characterization of the Vaccine Composition Described in the Present Invention (Vaccine Composition A)

1.1 Chromatographic Characterization of the Vaccine Composition Described in the Present Invention.

For the chromatographic characterization of the vaccine composition purified by ultrafiltration, homoligomeric conjugated hrEGF-hrEGF and rP64K-rP64K were used as indicators.

The chromatographic profiles shown by the homoligomeric conjugated (hrEGF-hrEGF and rP64K-rP64K) were compared with the chromatographic profile shown by the conjugated without purifying obtained by the chemical conjugation reaction among the proteins hrEGF and rP64K. In FIG. 1 are shown the profiles of the homoligomeric conjugates rP64K-rP64K and the profile obtained when carrying out the chemical conjugation between the proteins hrEGF and rP64K (chemical conjugated without purifying by ultra filtration. The circulated area belongs to the conjugated species hrEGF-rP64K. The profile of the conjugated rP64K-rP64K doesn't show total coincidence with this of the chemical conjugated hrEGF-rP64K due to the contribution of the hrEGF molecules conjugated to the rP64K.

In FIG. 2 are shown the results obtained after carrying out an un-naturalized electrophoresis in reduced conditions and a Western Blot of the vaccine composition purified by ultra filtration. The development was carried out with an anti-EGF antibody conjugated with alkaline phosphatase. The EGF is a protein of apparent molecular weight of 6 kDa so; it should be located in the inferior area of the gel. Its identification by means of immuno-detection with anti-EGF antibodies in the area corresponding to the proteins of molecular weigh apparently superiors to 6 kDa confirms that hrEGF molecules exist together to the rP64K in the area of the gel corresponding to the conjugated species hrEGF-rP64K.

When comparing the chromatographic profile of the chemical conjugated hrEGF-rP64 without purification with this of the homoligomeric conjugated hrEGF-hrEGF, it can be appreciated that exist a correspondence between both profiles. This evidence confirm that after the valley, exist a zone that corresponds to the hrEGF species conjugated in between them (EGF polymers) as well as free hrEGF (FIG. 3).

The molecular exclusion chromatographic profile (FIG. 4) of the vaccine composition object of the present invention shows that the area corresponding to the conjugated species hrEGF-rP64K, constitute more than the 90% of the total area of the chromatogram (shadow area) evidencing the high homogeneity of the described vaccine composition.

1.2. Conjugation Ratio Between the Proteins hrEGF and rP64K in the Vaccine Composition Described in the Present Invention With the objective of determining the conjugation ratio of the hrEGF and the rP64K in the vaccine composition, the moles of each one of the constitutive proteins were determined. For this it was taken a vaccine composition obtained from the 50 kDa ultrafiltration process, and the chromatographic fraction corresponding to the rhEGF-rP64K conjugated species was collected. These fractions were subjected to amino acid analysis.

The determination of the conjugation ratio was carried out by 2 methods.

1. A method was based in the estimation of the quantity of Phenylalanine (Phe) and Threonine (Thr) in the vaccine composition (aminoacid only present in the rP64K molecule). The quantities of these amino acids were used to determine the quantity of rP64K. Starting from this last one, and keeping in mind the total quantity of amino acids of the mixture, the quantity of EGF was determined.
2. The other method was based on the direct determination of the relative quantities of each protein, using the amino acid sequence and based in the quantification of those amino acids Asparagine+Aspartic (Asx), Glutamine+Glutamic (Glx), Glicine (Gly) and Alanine (Ala) (residues highly stable to the acid hydrolysis and commonly used in the quantification of proteins).

Tables 1 and 2 show the results obtained by each method.

TABLE 1

Determination of the conjugation ratio between the hrEGF and rP64K proteins carrying out the determination of aminoacidic composition of the vaccine composition purified by ultra filtration, based on the method of determination of the quantity of Phenilalanina (Phe) and Threonina (Thr)

| Mean quantity of rP64K | Mean quantity of hrEGF | Mean ratio of conjugation |
|---|---|---|
| 12.07 nmoles | 23.13 nmoles | 1.92 |

TABLE 2

Determination of the conjugation ratio between the hrEGF and rP64K proteins carrying out the determination of amino acid composition of the vaccine composition purified by ultrafiltration, based on the method of determination of the relative quantities of the amino acids Asparagine + Aspartic (Asx), Glutamine + Glutamic (Glx), Glicine (Gly) and Alanine (Ala)

| Protein | Quantity of protein | Conjugation ratio |
|---|---|---|
| rP64K | 12.04 nmoles | 2.00 |
| hrEGF | 24.05 nmoles | |

The results obtained by both methods shows correspondence in the estimate of the conjugation ratio among the hrEGF:rP64K proteins for the vaccine composition described in the present invention. The calculated ratio of conjugation was of (1:2), which means 2 hrEGF molecules for each rP64K molecule.

1.3. The Peptide Maps Characterizing the Vaccine Composition Described in the Present Invention With the objective of characterizing the structure of the vaccine composition presented in the present invention and to evidence the reproducibility of the procedure it was developed and characterized the peptide map obtained after the digestion of the conjugated fractions hrEGF-rP64K with the endoprotease Glu-C. Each one of the fractions of the obtained map were identified and sequenced by Mass Spectrometry.

FIG. 5 shows the peptide maps obtained starting from two vaccine compositions obtained independently, where a great similarity is appreciated in the peptides that appeared and in its relative proportion. The reproducibility among those peptide maps obtained starting from both vaccine compositions is an indicative of the control that exist over the conditions in which the procedures of chemical conjugation and purification (described in the present invention) happen.

The identification of the peptides contained in each fraction of the map was obtained by the analysis of each one of them by the MALDI method (Matrix Assisted Laser Desorption Ionization) and by the ESI-MS method (Electrospray Ionization/Electronebulization by ionization). In Table 3 the SEQ. ID NOS. of the major peptides are shown as follows.

TABLE 3

Aminoacidic composition of the major peptides obtained after the digestion of the EGF-P64K conjugated fraction with the endoprotease Glu-C. The amino acid composition was determined by MALDI and ESI-MS.

| Peak | SEQ. ID No. | Peptides |
|---|---|---|
| HG05 | 1 | LDID |
|  | 2 | QAAPTGE |
| HG06 | 3 | SIGMAAE |
|  | 4 | AEGTAAAPKAE |
| HG09 | 5 | KISE |
| HG11 | 6 | AAAAPAQEAPKAA |
|  | 7 | GANAPKEPQRYD |
| HG14 | 8 | VKVKVGDKISE |
| HG15 | 9 | VAWVGE |
| HG16 | 10 | VAWVGETE |
|  | 11 | VSLTAGDAYE |
| HG17 | 12 | VCLAIE |
| HG18 | 13 | VRHLAANGIKYPEPE |
| HG19 | 14 | AAAAPAQEAPKAAAPAPQAAQFG |
| HG20 | 15 | LKVPDIGGHE |
|  | 16 | RVIPGVAYTSPE |
|  | 17 | TGRIIGGGIVGPN |
| HG21 | 18 | KAGVAVTDRGFIE |
|  | 19 | LIFDAE |
|  | 20 | GGPGGYSAAFAAADE |
| HG22 | 21 | ARVIPGVAYTSPE |
|  | 22 | GLKVAIVE |
| HG23 | 23 | AAAAPAQEAPKAAAPAPQAAQFGGSADAEYD |
|  | 24 | MGCDAADIGKTIHPHPTLGE |
|  | 25 | PKEPQRYDAVLVAAGR |

TABLE 3-continued

Aminoacidic composition of the major peptides obtained after the digestion of the EGF-P64K conjugated fraction with the endoprotease Glu-C. The amino acid composition was determined by MALDI and ESI-MS.

| Peak | SEQ. ID No. | Peptides |
|---|---|---|
| HG24 | 26 | NVDIIAVE |
|  | 27 | YDVVVLG |
| HG25 | 28 | AVLVAAGRAPNGKLISAE |
|  | 29 | TGRIIGGGIVGPNGGDMIGE |
| HG26 | 30 | VRHLAANGIKYPEPELD |
| HG27 | 31 | RCQYRDLKWWE |
| HG28 | 32 | GGLIVVVE |
| HG29 | 33 | YRFDNIMVNTKTVAVEPKED |
| HG30 | 34 | AIGDIVGQPMLAHKAVHE |
| HG31 | 35 | ALDKYACNCVVGYIGE |
| HG32 | 36 | LDIDMLRAY |
|  | 37 | MDVPAEVAGVVKE |
| HG33 | 38 | GYCLHDGVCMYIE |
| HG34 | 39 | NCAGHKAYFDARVIPGVAYTSPE |
| HG35 | 40 | GANAPKEPQRYDAVLVAAGRAPNGKLISAE |
| HG36 | 41 | VIDEVRHLAANGIKYPE |
| HG37 | 42 | MGTVYSTLGSRLDVVE |
| HG38 | 43 | IIGGGIIGLE |
|  | 44 | MDVPAEVAGVVKEVK |
|  | 45 | NSDSECPLSHDGYCLHDGVCMYIE |
| HG39 | 46 | VVVLGGGPGGYSAAFAAADE |
| HG41 | 47 | LKVPDIGGHENVDIIAVE |
| HG42 | 48 | RCQYRDLKWWEL |
| HG43 | 49 | VDKQMRTNVPHIYAIGDIVGQPMLAHKAVHE |
|  | 50 | ASGRAIANGCDNGFTKLIFDAE |
| HG47 | 51 | YRFDNIMVNTKTVAVEPKEDGVYVTFE |
|  | 52 | AIANGCDNGFTKLIFDAE |
| HG48 | 53 | RYKTLGGVCLNVGCIPSKALLHNAAVIDE |
| HG49 | 54 | VNVGDTIAVDDTLITLD |
|  | 55 | IVGQPMLAHKAVHEGHVAAENCAGHKAYFD |
|  | 56 | NGFTKLIFDAETGRIIGGGIVGPNGGDMIGE |
| HG50 | 57 | TGRIIGGGIVGPNGGDMIGEVCLAIEMGCD |

Example 2

Immunogenicity of the Vaccine Composition Described in the Present Invention In this example, the biological activity assay is carried out for evaluation of the immunogenicity of the vaccine composition previously described (vaccine composition A), in comparison with a vaccine composition described in EP 0657 175 (vaccine composition B).

The assay was carried out with the inoculation of 10 mice with an unique dose of 200 µL of a water in oil emulsion (50/50% v/v) of the immunogens (conventional vaccine composition obtained by dialysis, vaccine composition obtained by purification with ultrafiltration membrane and permeated obtained from purification process by UF/DF where conjugated species hrEGF-hrEGF are present), with the adjuvant MONTANIDE, a mixture of a mineral oil and a surfactant. ISA 51. The protein dose applied for each immunogen is referred in Table 4.

In the 14 days following the inoculation, serum extraction from the animals and the evaluation of the anti-EGF antibody titers by means of an ELISA was performed. The positive criterion for the assay was that the measured optical density at 405 nm must be higher than the double of the mean value obtained for the blank, which is obtained by adding to the well blockade buffer instead of the serum. The test of Mann-Whitney was applied to the analysis of the data, by using a statistical program.

TABLE 4

Immunogens evaluated and protein concentrations to be inoculated by animal according to the corresponding for the of biological activity assay.

| Immunogens | Protein concentration (Lowry) |
|---|---|
| Vaccine composition A | 1.5 mg/mL |
| Vaccine composition B | 1.5 mg/mL |
| Homopolymeric conjugates of hrEGF and hrEGF free obtained from the purification by UF/DF of the vaccine composition A | 0.6 mg/mL |

In FIG. 6, the results of the biological activity assay are shown as evidences of the immunogenic activity of each evaluated immunogen. The components of the immunogen corresponding to the homopolymeric hrEGF conjugates and free hrEGF, doesn't show relevant biological activity, because their response is at the level of the positive criteria for the assay or inferior. These results verify the hypothesis that the EGF by itself does not induce an immunogenic response.

The statistical analysis of all the results when applying the "Mann-Whitney Test".

(Table 5) showed highly significant differences for the anti-hrEGF antibody titers 1/1000 with p=0.0004 and for the 1/100 titer with p=0.0006 for group of animals inoculated with the vaccine composition A as compared to the titers reached for the group of animals inoculated with the vaccine composition B. This indicates that the vaccine composition A, purified by means of an ultrafiltration membrane has bigger immunogenic activity per milligram of protein that the vaccine composition B, obtained by the purification method based on dialysis membrane.

The vaccine composition A produces an increment of the concentration of antibodies anti EGF (at 1/1000 dilution) 10 times higher as compared with this reached when immunizing with the conjugates corresponding to polymeric hrEGF and free hrEGF.

When comparing with the vaccine composition previously described in EP 0657175, the vaccine composition described in the present invention produced an increment of twice the concentration of anti-rhEGF antibodies.

TABLE 5

Statistical report; the Mann-Whitney test used to evaluate the immunogenicity of both vaccine compositions through the anti-hrEGF antibody titers in mice.

Statistical analysis about the anti-hrEGF antibody titers in mice. (dilution 1/1000)
Mann-Whitney Test and CI: G1 1/1000; G3 1/1000

|  |  | N | Median |
|---|---|---|---|
| G1 (Prepared Vaccine B) | 1/1000 | 20 | 0.4300 |
| G3 (Prepared Vaccine A) | 1/1000 | 20 | 0.7120 |

Point estimate for ETA1-ETA2 is −0.3115
95.0 Percent CI for ETA1-ETA2 is (−0.4500; −0.1790)
W = 278.0
Test of ETA1 = ETA2 vs ETA1 not = ETA2 is significant at 0.0004
The test is significant at 0.0004 (adjusted for ties)
Statistical analysis about the anti-hrEGF antibody titers in mice. (dilution 1/100)
Mann-Whitney Test and CI: G1 1/100; G3 1/100

|  |  | N | Median |
|---|---|---|---|
| G1 (Conventionally prepared vaccine ) | 1/100 | 20 | 1.0785 |
| G3 (Vaccine prepared by ultrafiltration) | 1/100 | 20 | 1.3040 |

Point estimate for ETA1-ETA2 is −0.2590
95.0 Percent CI for ETA1-ETA2 is (−0.4389; −0.1149)
W = 282.5
Test of ETA1 = ETA2 vs ETA1 not = ETA2 is significant at 0.0006
The test is significant at 0.0006 (adjusted for ties)

Example 3

Evaluation of the Clinical Efficacy of the Vaccine Composition Disclosed by the Present Invention in the Treatment of Lung Tumors of Epithelial Origin The objective of this example is to evaluate in patients the immunogenicity elicited by the Vaccine composition A in comparison with the immunogenicity induced by the Vaccine composition B obtained by the method of purification by dialysis.

In this study, patients with advanced stages Non Small Cell Lung Cancer (NSCLC) tumors were treated. Two groups of patients were defined (patients vaccinated with the preparation B and patients vaccinated with the preparation A described in the present invention). The vaccine composition dose per patient in each group was as follows: Patients vaccinated with the preparation B received 1.2 mg of total protein per immunization site, while patients vaccinated with the preparation B received 0.6 mg of total proteins per immunization site. For both groups the immunization sites were 4. All patients received oncospecific therapy, at least 4 weeks before starting the trial. Immunizations were performed by intramuscular route and continued occurring monthly.

The humoral immune response of both groups of patients was evaluated through their serum. The main variable for evaluating the results was the specific anti-EGF antibody titer. This parameter was determined through an ELISA. The positive values were those that gave optical density readings 2 times higher than the negative control. The reported antibody titer is the maximal dilution of positive serum.

The analysis of the immune response for patients in each group, as represented in Table 6, showed that the geometric mean of the maximal antibody titer in the group of patients treated with the preparation A corresponds to 1:56421, while in the group of patients immunized with the preparation B was of 1:23515. That means that the vaccine composition described in the present invention elicited an increase of twice the geometric mean of the maximal antibody titers as compared with the titers reached with the preparation B.

Historically, the unimmunized patients show an anti-autologous EGF antibody titer of 1:500. Therefore the vaccine composition described in the present invention (vaccine composition A) causes an increase of at least 100 times the title of anti-EGF antibodies in non-immunized patients.

TABLE 6

Result of the analysis of the geometric mean of immunogenicity for both vaccine compositions through the measurement of anti-EGF antibody titers in patient's serum.

|  | Total of patients | Geometric mean |
|---|---|---|
| Vaccine composition A | 11 | 56421 |
| Vaccine composition B | 9 | 23515 |

It is important to stress that the group of patients immunized with the Vaccine composition A, described in the present invention, showed a superior geometric mean of the anti-EGF antibody titers receiving half of the quantity of total proteins per immunization (2.4 mg) that the one received by the group of patients immunized with the Vaccine composition B (4.8 mg of total proteins), what constitutes a surprising result. These results evidence that the excess of autologous protein hrEGF, either in form of polymers or free, doesn't contribute to more immunogenicity of the vaccine composition, but it dilutes the immunological action of the chemical conjugated hrEGF-rP64K.

Example 4

Obtaining the Vaccine Composition Adjusted to Different Potency (Concentration of Total Proteins Per Vial)

With the purpose of demonstrating the capacity to obtain vaccine compositions with different potency (concentrations of total proteins per vial), it was carried out the purification methodology like it is described below:

Assay 1: When concluding the diafiltration the purified chemical conjugated was concentrated until a final concentration of proteins of 2 mg/mL.

Assay 2: When concluding the diafiltration the purified chemical conjugated was concentrated until a final concentration of proteins of 5 mg/mL.

Assay 3: When concluding the diafiltration the purified chemical conjugated was concentrated until a final concentration of proteins of 12 mg/mL.

In all the assays the total volume of chemical conjugates employee was 1500 mL, it was operated at a trans-membrane pressure of 1.5 bar and 7 tampon solution changes were carried out during the diafiltration. For the realization of this evaluation two selection criteria were established:

The first one was to reach a homogeneity percent of the vaccine composition >80%.

The second criterion was the non-presence of precipitated proteins during the purification operation.

The results, presented in Table 7, shows the vaccine compositions adjusted at different protein concentrations per mL, guaranteeing high levels of homogeneity (90.92%, 96.79% and, 95.50% of species conjugated hrEGFrP64K) and without producing precipitation of proteins.

TABLE 7

Values corresponding to the percent of homogeneity in the vaccine compositions adjusted to different final protein concentrations.

| Protein concentration | Percent of homogeneity of the vaccine composition |
|---|---|
| 2 mg/mL | 92.00% |
| 5 mg/mL | 96.79% |
| 12 mg/mL | 95.50% |

Example 5

Glutaraldehyde Removal from the Vaccine Composition of the Present Invention

To evaluate the removal of the conjugation agent (glutaraldehyde) it was quantified the residual glutaraldehyde contents in the vaccine composition B and in the vaccine composition A, by means of a reverse phase chromatographic separation method (HPLC-RP), employing a C-8 column.

This method required firstly, the precipitation of the protein contained in the samples with perchloric acid and later a reaction with phenylhydracine.

FIG. 7 shows that the residual content of this impurity in both vaccine compositions was smaller than 0.2 ug/mL or smaller than 0.002 ppm, (highest concentration limit established for this impurity) from an initial concentration of 530 mg/mL or 530 ppm. Even when both preparations fulfill the established specification for this impurity, FIG. 7 illustrates that the vaccine composition A (obtained when applying the ultrafiltration method for purification of the chemical conjugated) possesses an inferior content of glutaraldehyde, what contributes to a great security for the patient that uses this vaccine composition.

Conventional vaccine composition, vaccine composition purified by ultrafiltration and permeate proceeding from the ultrafiltration purification method. X axis corresponds to the sera dilutions from each animal and the Y axis represents the value of optical density at 405 nm of each sample, as indicator of the protein concentration.

Figure 1:
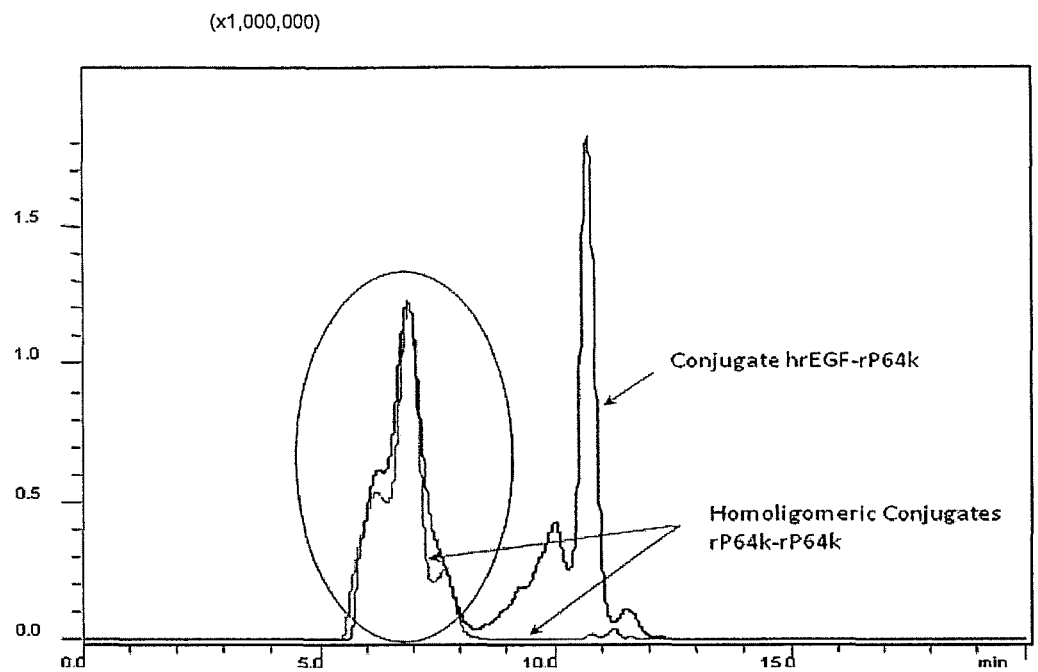
FIG. 1. Shows the overlapping of the chromatogram of a homoligomeric conjugated rP64K-rP64K with the chromatogram of a not purified chemical conjugated EGF-P64K. In the circle is shown the coincidence of profiles between both chromatograms. The X axis represents the time until elution for each component of the sample and the Y axis represents the value of intensity at 216 nm for each component of the sample, as indicator of protein concentration.
Figure 2:
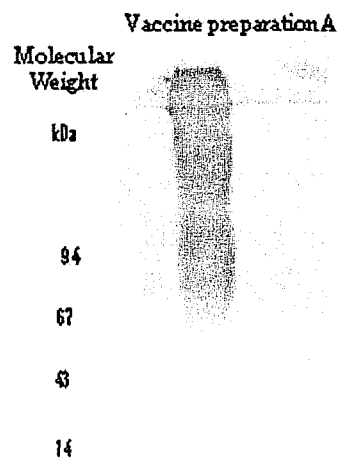
FIG. 2. Immuno-detection with an anti EGF antibody conjugated with alkalyne phosphatase, after SDS-PAGE electrophoretic separation for the vaccine composition obtained by ultrafiltration Line 1: Molecular weight marker, Line 2 vaccine composition.
Figure 3:
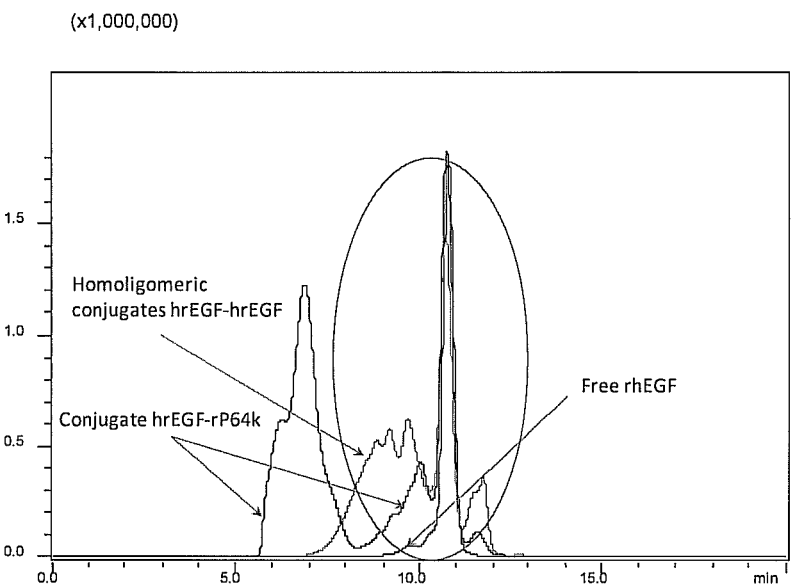
FIG. 3. Shows the overlapping of the chromatograms corresponding to the homoligomeric hrEGF-hrEGF conjugated and of the chromatogram corresponding to a chemical conjugated hrEGF-rP64K without purify. In the circle is shown the coincidence of species among both chromatograms. The X axis represents the time for elution of each component and the Y axis represents the value of intensity at 216 nm of each sample component, as indicator of the protein concentration.
Figure 4:
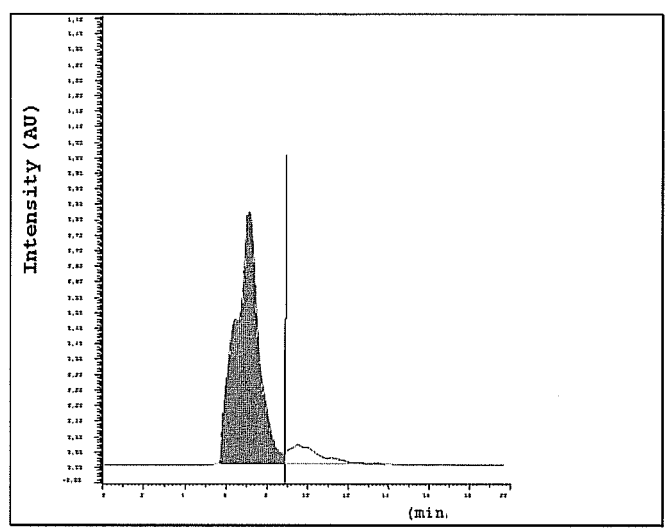
FIG. 4. Chromatographic profile corresponding to the vaccine disclosed by the present invention. The shady area corresponds to the hrEGF-rP64K conjugated species. The X axis represents the time for elution of each fraction and the Y axis represents the value of intensity at 216 nm of each component in the sample, as indicator of the protein concentration.
Figure 5:
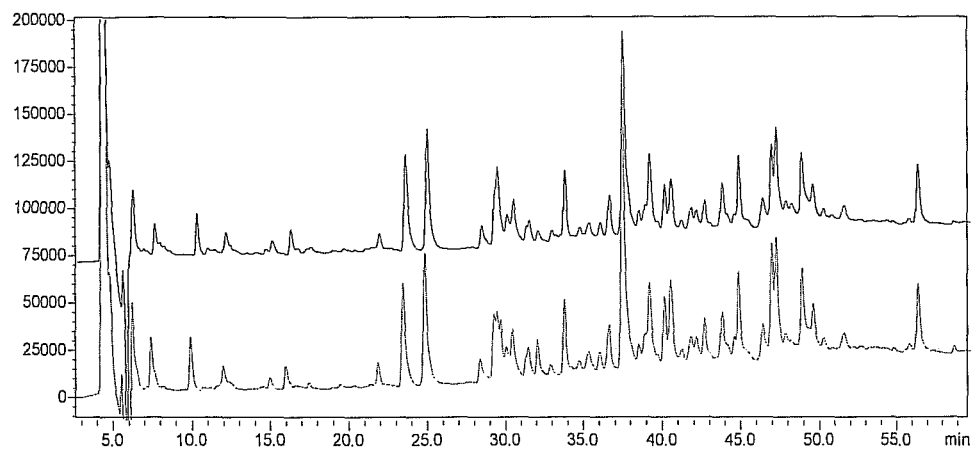
FIG. 5. The peptide map of the chromatographic fraction corresponding to the conjugated hrEGF-rP64K. These are the results from two vaccine compositions purified independently by an ultrafiltration membrane. The X axis represents the time and the Y axis represents the units of mili intensity.
Figure 6:
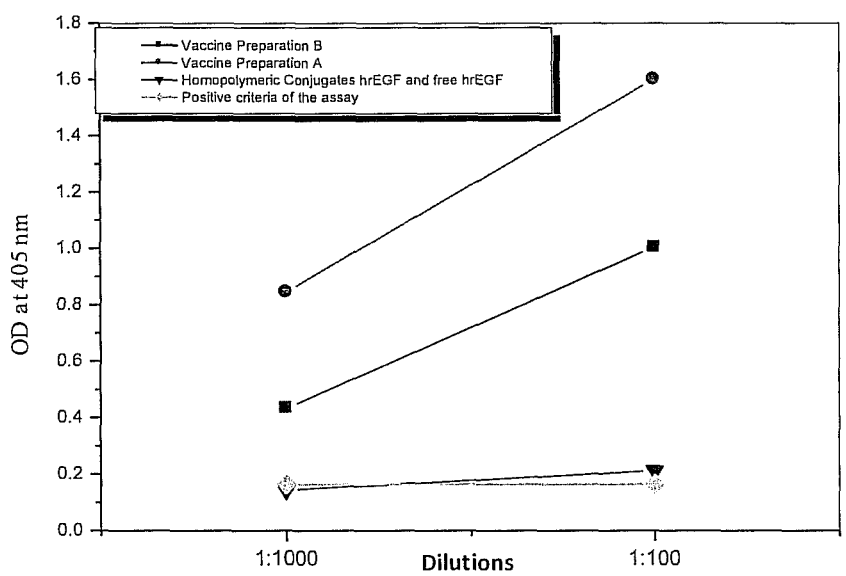
FIG. 6. Anti-hrEGF antibody titers in mice immunized with different immunogens.
Figure 7:
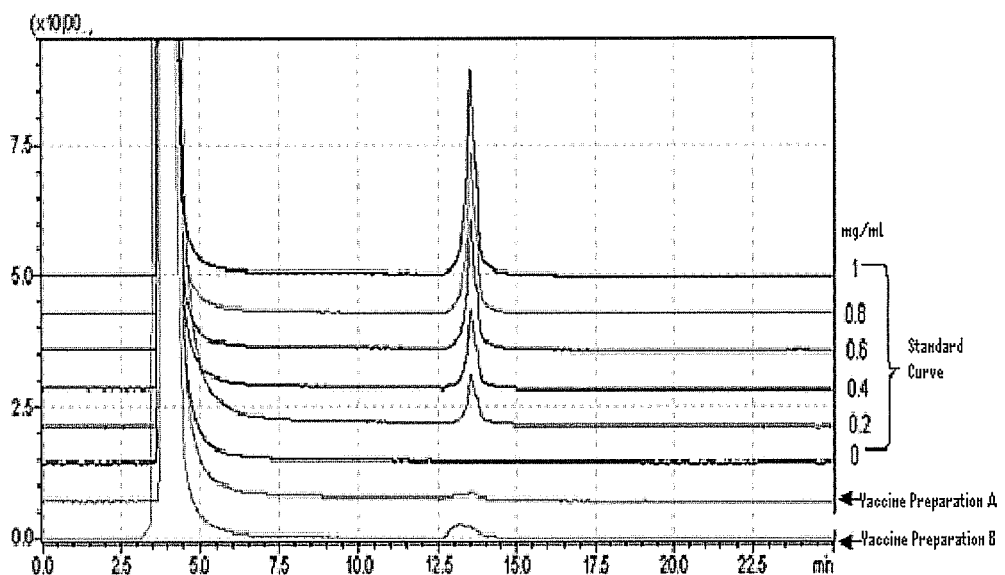

FIG. 7. Chromatographic profile by HPLC-RP obtained during the quantification of the residual glutaraldehyde content of the vaccine composition obtained by the purification method using 50 kDa ultrafiltration membranes (vaccine composition A) and for the vaccine composition using dialysis purification method (vaccine composition B).

SUMMARY OF THE INVENTION

The present invention relates to the biotechnological field and particularly to the human health. More particularly, the present invention relates to a vaccine composition for therapeutic use in cancer patients.

The vaccine composition of the present invention has as active principle a chemical conjugated between the human recombinant Epidermal Growth Factor (hrEGF) and the P64K recombinant protein. In another embodiment, the present invention relates to the conjugation procedure to obtain, a chemical conjugated under controlled and reproducible parameters.

In a preferred embodiment, the present invention relates to the procedure for purifying the chemical conjugated with a higher purity of the therapeutical vaccine composition, and a surprisingly increased immunogenic activity, inducing a significant increase of the anti-EGF antibody titers in humans.

Additionally the present invention provides the methodology to obtain a vaccine composition in several dose presentations (total milligrams of conjugated EGF-P64K/vial). The versatility of the dose presentation allows increasing the immunization dose per patient, without increasing the frequency of injections and/or immunization sites.

Besides, the present invention relates to a sanitary procedure for obtaining a vaccine composition for parenteral route in the cancer therapy.

What is claimed is:

1. A method for making a vaccine composition for treating lung cancer, said method comprising: ultrafiltrating a conjugated hrEGF-rP64K protein, wherein after ultrafiltration a homogeneous mix of the conjugated hrEGF-rP64K protein is obtained, and wherein each rP64K carrier protein molecule is bound to two hrEGF molecules, the conjugation ratio between the rP64K carrier and the hrEGF protein is 12.04: 24.05, the total protein is in the range of 1-12 mg/mL and constitutes more than 90% of the total area of a chromatogram.

2. The method of claim 1, wherein the homogenous mix of the conjugated hrEGF-rP64K protein is free of glutaraldehyde.

3. The method of claim 1, wherein the ultrafiltration concentration comprises a 100 kDa membrane filtration concentration.

4. The method of claim 1, wherein the homogenous mix of the conjugated hrEGF-rP64K protein induces an increase of at least 100 times the anti-EGF antibody titers in the serum of humans.

5. The method of claim 1, wherein the vaccine composition allows increasing the treatment dose for a patient without increasing the frequency of immunization or number of immunization sites.

6. The method of claim 1, further comprising adding the adjuvant after the ultrafiltering.

7. The method of claim 6, wherein the adjuvant consists of a mineral oil and a surfactant.

* * * * *

SEQUENCE LISTING

```
<160> NUMBER OF SEQ ID NOS: 57

<210> SEQ ID NO 1
<211> LENGTH: 4
<212> TYPE: PRT
<213> ORGANISM: Artificial Sequence
<220> FEATURE:
<223> OTHER INFORMATION: recombinant genetic material from human/
      bacterial

<400> SEQUENCE: 1

Leu Asp Ile Asp
1

<210> SEQ ID NO 2
<211> LENGTH: 7
<212> TYPE: PRT
<213> ORGANISM: Artificial Sequence
<220> FEATURE:
<223> OTHER INFORMATION: recombinant genetic material from human/
      bacterial

<400> SEQUENCE: 2

Gln Ala Ala Pro Thr Gly Glu
1               5

<210> SEQ ID NO 3
<211> LENGTH: 7
<212> TYPE: PRT
<213> ORGANISM: Artificial Sequence
<220> FEATURE:
<223> OTHER INFORMATION: recombinant genetic material from human/
      bacterial

<400> SEQUENCE: 3

Ser Ile Gly Met Ala Ala Glu
1               5
```

```
<210> SEQ ID NO 4
<211> LENGTH: 11
<212> TYPE: PRT
<213> ORGANISM: Artificial Sequence
<220> FEATURE:
<223> OTHER INFORMATION: recombinant genetic material from human/
      bacterial

<400> SEQUENCE: 4

Ala Glu Gly Thr Ala Ala Ala Pro Lys Ala Glu
1               5                   10

<210> SEQ ID NO 5
<211> LENGTH: 4
<212> TYPE: PRT
<213> ORGANISM: Artificial Sequence
<220> FEATURE:
<223> OTHER INFORMATION: recombinant genetic material from human/
      bacterial

<400> SEQUENCE: 5

Lys Ile Ser Glu
1

<210> SEQ ID NO 6
<211> LENGTH: 13
<212> TYPE: PRT
<213> ORGANISM: Artificial Sequence
<220> FEATURE:
<223> OTHER INFORMATION: recombinant genetic material from human/
      bacterial

<400> SEQUENCE: 6

Ala Ala Ala Ala Pro Ala Gln Glu Ala Pro Lys Ala Ala
1               5                   10

<210> SEQ ID NO 7
<211> LENGTH: 12
<212> TYPE: PRT
<213> ORGANISM: Artificial Sequence
<220> FEATURE:
<223> OTHER INFORMATION: recombinant genetic material from human/
      bacterial

<400> SEQUENCE: 7

Gly Ala Asn Ala Pro Lys Glu Pro Gln Arg Tyr Asp
1               5                   10

<210> SEQ ID NO 8
<211> LENGTH: 11
<212> TYPE: PRT
<213> ORGANISM: Artificial Sequence
<220> FEATURE:
<223> OTHER INFORMATION: recombinant genetic material human/
      bacterial

<400> SEQUENCE: 8

Val Lys Val Lys Val Gly Asp Lys Ile Ser Glu
1               5                   10

<210> SEQ ID NO 9
<211> LENGTH: 6
<212> TYPE: PRT
<213> ORGANISM: Artificial Sequence
<220> FEATURE:
<223> OTHER INFORMATION: recombinant genetic material human/bacterial

<400> SEQUENCE: 9
```

```
Val Ala Trp Val Gly Glu
1               5

<210> SEQ ID NO 10
<211> LENGTH: 8
<212> TYPE: PRT
<213> ORGANISM: Artificial Sequence
<220> FEATURE:
<223> OTHER INFORMATION: recombinant genetic material human/bacterial

<400> SEQUENCE: 10

Val Ala Trp Val Gly Glu Thr Glu
1               5

<210> SEQ ID NO 11
<211> LENGTH: 10
<212> TYPE: PRT
<213> ORGANISM: Artificial Sequence
<220> FEATURE:
<223> OTHER INFORMATION: recombinant genetic material human/bacterial

<400> SEQUENCE: 11

Val Ser Leu Thr Ala Gly Asp Ala Tyr Glu
1               5                   10

<210> SEQ ID NO 12
<211> LENGTH: 6
<212> TYPE: PRT
<213> ORGANISM: Artificial Sequence
<220> FEATURE:
<223> OTHER INFORMATION: recombinant genetic material from human/
      bacterial

<400> SEQUENCE: 12

Val Cys Leu Ala Ile Glu
1               5

<210> SEQ ID NO 13
<211> LENGTH: 15
<212> TYPE: PRT
<213> ORGANISM: Artificial Sequence
<220> FEATURE:
<223> OTHER INFORMATION: recombinant genetic material from human/
      bacterial

<400> SEQUENCE: 13

Val Arg His Leu Ala Ala Asn Gly Ile Lys Tyr Pro Glu Pro Glu
1               5                   10                  15

<210> SEQ ID NO 14
<211> LENGTH: 23
<212> TYPE: PRT
<213> ORGANISM: Artificial Sequence
<220> FEATURE:
<223> OTHER INFORMATION: recombinant genetic material from human/
      bacterial

<400> SEQUENCE: 14

Ala Ala Ala Ala Pro Ala Gln Glu Ala Pro Lys Ala Ala Ala Pro Ala
1               5                   10                  15

Pro Gln Ala Ala Gln Phe Gly
            20

<210> SEQ ID NO 15
<211> LENGTH: 10
<212> TYPE: PRT
```

<213> ORGANISM: Artificial Sequence
<220> FEATURE:
<223> OTHER INFORMATION: recombinant genetic material from human/
      bacterial

<400> SEQUENCE: 15

Leu Lys Val Pro Asp Ile Gly Gly His Glu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: recombinant genetic material from human/
      bacterial

<400> SEQUENCE: 16

Arg Val Ile Pro Gly Val Ala Tyr Thr Ser Pro Glu
1               5                   10

<210> SEQ ID NO 17
<211> LENGTH: 13
<212> TYPE: PRT
<213> ORGANISM: Artificial Sequence
<220> FEATURE:
<223> OTHER INFORMATION: recombinant genetic material from human/
      bacterial

<400> SEQUENCE: 17

Thr Gly Arg Ile Ile Gly Gly Gly Ile Val Gly Pro Asn
1               5                   10

<210> SEQ ID NO 18
<211> LENGTH: 13
<212> TYPE: PRT
<213> ORGANISM: Artificial Sequence
<220> FEATURE:
<223> OTHER INFORMATION: recombinant genetic material from human/
      bacterial

<400> SEQUENCE: 18

Lys Ala Gly Val Ala Val Thr Asp Arg Gly Phe Ile Glu
1               5                   10

<210> SEQ ID NO 19
<211> LENGTH: 6
<212> TYPE: PRT
<213> ORGANISM: Artificial sequence
<220> FEATURE:
<223> OTHER INFORMATION: recombinant genetic material from human/
      bacterial

<400> SEQUENCE: 19

Leu Ile Phe Asp Ala Glu
1               5

<210> SEQ ID NO 20
<211> LENGTH: 15
<212> TYPE: PRT
<213> ORGANISM: Artificial Sequence
<220> FEATURE:
<223> OTHER INFORMATION: recombinant genetic material from human/
      bacterial

<400> SEQUENCE: 20

Gly Gly Pro Gly Gly Tyr Ser Ala Ala Phe Ala Ala Ala Asp Glu
1               5                   10                  15

```
<210> SEQ ID NO 21
<211> LENGTH: 13
<212> TYPE: PRT
<213> ORGANISM: Artificial Sequence
<220> FEATURE:
<223> OTHER INFORMATION: recombinant genetic material from human/
      bacterial

<400> SEQUENCE: 21

Ala Arg Val Ile Pro Gly Val Ala Tyr Thr Ser Pro Glu
1               5                   10

<210> SEQ ID NO 22
<211> LENGTH: 8
<212> TYPE: PRT
<213> ORGANISM: Artificial Sequence
<220> FEATURE:
<223> OTHER INFORMATION: recombinant genetic material from human/
      bacterial

<400> SEQUENCE: 22

Gly Leu Lys Val Ala Ile Val Glu
1               5

<210> SEQ ID NO 23
<211> LENGTH: 31
<212> TYPE: PRT
<213> ORGANISM: Artificial Sequence
<220> FEATURE:
<223> OTHER INFORMATION: recombinant genetic material from human/
      bacterial

<400> SEQUENCE: 23

Ala Ala Ala Ala Pro Ala Gln Glu Ala Pro Lys Ala Ala Ala Pro Ala
1               5                   10                  15

Pro Gln Ala Ala Gln Phe Gly Gly Ser Ala Asp Ala Glu Tyr Asp
                20                  25                  30

<210> SEQ ID NO 24
<211> LENGTH: 20
<212> TYPE: PRT
<213> ORGANISM: Artificial Sequence
<220> FEATURE:
<223> OTHER INFORMATION: recombinant genetic material from human/
      bacterial

<400> SEQUENCE: 24

Met Gly Cys Asp Ala Ala Asp Ile Gly Lys Thr Ile His Pro His Pro
1               5                   10                  15

Thr Leu Gly Glu
                20

<210> SEQ ID NO 25
<211> LENGTH: 16
<212> TYPE: PRT
<213> ORGANISM: Artificial Sequence
<220> FEATURE:
<223> OTHER INFORMATION: recombinant genetic material from human/
      bacterial

<400> SEQUENCE: 25

Pro Lys Glu Pro Gln Arg Tyr Asp Ala Val Leu Val Ala Ala Gly Arg
1               5                   10                  15

<210> SEQ ID NO 26
```

```
<211> LENGTH: 8
<212> TYPE: PRT
<213> ORGANISM: Artificial Sequence
<220> FEATURE:
<223> OTHER INFORMATION: recombinant genetic material from human/
      bacterial

<400> SEQUENCE: 26

Asn Val Asp Ile Ile Ala Val Glu
1               5

<210> SEQ ID NO 27
<211> LENGTH: 7
<212> TYPE: PRT
<213> ORGANISM: Artificial Sequence
<220> FEATURE:
<223> OTHER INFORMATION: recombinant genetic material from human/
      bacterial

<400> SEQUENCE: 27

Tyr Asp Val Val Val Leu Gly
1               5

<210> SEQ ID NO 28
<211> LENGTH: 18
<212> TYPE: PRT
<213> ORGANISM: Artificial Sequence
<220> FEATURE:
<223> OTHER INFORMATION: recombinant genetic material from human/
      bacterial

<400> SEQUENCE: 28

Ala Val Leu Val Ala Ala Gly Arg Ala Pro Asn Gly Lys Leu Ile Ser
1               5                   10                  15

Ala Glu

<210> SEQ ID NO 29
<211> LENGTH: 20
<212> TYPE: PRT
<213> ORGANISM: Artificial Sequence
<220> FEATURE:
<223> OTHER INFORMATION: recombinant genetic material from human/
      bacterial

<400> SEQUENCE: 29

Thr Gly Arg Ile Ile Gly Gly Gly Ile Val Gly Pro Asn Gly Gly Asp
1               5                   10                  15

Met Ile Gly Glu
            20

<210> SEQ ID NO 30
<211> LENGTH: 17
<212> TYPE: PRT
<213> ORGANISM: Artificial Sequence
<220> FEATURE:
<223> OTHER INFORMATION: recombinant genetic material from human/
      bacterial

<400> SEQUENCE: 30

Val Arg His Leu Ala Ala Asn Gly Ile Lys Tyr Pro Glu Pro Glu Leu
1               5                   10                  15

Asp

<210> SEQ ID NO 31
<211> LENGTH: 11
<212> TYPE: PRT
```

```
<213> ORGANISM: Artificial Sequence
<220> FEATURE:
<223> OTHER INFORMATION: recombinant genetic material from human/
      bacterial

<400> SEQUENCE: 31

Arg Cys Gln Tyr Arg Asp Leu Lys Trp Trp Glu
1               5                   10

<210> SEQ ID NO 32
<211> LENGTH: 8
<212> TYPE: PRT
<213> ORGANISM: Artificial Sequence
<220> FEATURE:
<223> OTHER INFORMATION: recombinant genetic material from human/
      bacterial

<400> SEQUENCE: 32

Gly Gly Leu Ile Val Val Val Glu
1               5

<210> SEQ ID NO 33
<211> LENGTH: 20
<212> TYPE: PRT
<213> ORGANISM: Artificial Sequence
<220> FEATURE:
<223> OTHER INFORMATION: recombinant genetic material from human/
      bacterial

<400> SEQUENCE: 33

Tyr Arg Phe Asp Asn Ile Met Val Asn Thr Lys Thr Val Ala Val Glu
1               5                   10                  15

Pro Lys Glu Asp
            20

<210> SEQ ID NO 34
<211> LENGTH: 18
<212> TYPE: PRT
<213> ORGANISM: Artificial Sequence
<220> FEATURE:
<223> OTHER INFORMATION: recombinant genetic material from human/
      bacterial

<400> SEQUENCE: 34

Ala Ile Gly Asp Ile Val Gly Gln Pro Met Leu Ala His Lys Ala Val
1               5                   10                  15

His Glu

<210> SEQ ID NO 35
<211> LENGTH: 16
<212> TYPE: PRT
<213> ORGANISM: Artificial Sequence
<220> FEATURE:
<223> OTHER INFORMATION: recombinant genetic material from human/
      bacterial

<400> SEQUENCE: 35

Ala Leu Asp Lys Tyr Ala Cys Asn Cys Val Val Gly Tyr Ile Gly Glu
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: recombinant genetic material from human/
      bacterial
```

```
<400> SEQUENCE: 36

Leu Asp Ile Asp Met Leu Arg Ala Tyr
1               5

<210> SEQ ID NO 37
<211> LENGTH: 13
<212> TYPE: PRT
<213> ORGANISM: Artificial Sequence
<220> FEATURE:
<223> OTHER INFORMATION: recombinant genetic material human/bacterial

<400> SEQUENCE: 37

Met Asp Val Pro Ala Glu Val Ala Gly Val Val Lys Glu
1               5                   10

<210> SEQ ID NO 38
<211> LENGTH: 13
<212> TYPE: PRT
<213> ORGANISM: Artificial Sequence
<220> FEATURE:
<223> OTHER INFORMATION: recombinant genetic material from human/
      bacterial

<400> SEQUENCE: 38

Gly Tyr Cys Leu His Asp Gly Val Cys Met Tyr Ile Glu
1               5                   10

<210> SEQ ID NO 39
<211> LENGTH: 23
<212> TYPE: PRT
<213> ORGANISM: Artificial Sequence
<220> FEATURE:
<223> OTHER INFORMATION: recombinant genetic material from human/
      bacterial

<400> SEQUENCE: 39

Asn Cys Ala Gly His Lys Ala Tyr Phe Asp Ala Arg Val Ile Pro Gly
1               5                   10                  15

Val Ala Tyr Thr Ser Pro Glu
            20

<210> SEQ ID NO 40
<211> LENGTH: 30
<212> TYPE: PRT
<213> ORGANISM: Artificial Sequence
<220> FEATURE:
<223> OTHER INFORMATION: recombinant genetic material from human/
      bacterial

<400> SEQUENCE: 40

Gly Ala Asn Ala Pro Lys Glu Pro Gln Arg Tyr Asp Ala Val Leu Val
1               5                   10                  15

Ala Ala Gly Arg Ala Pro Asn Gly Lys Leu Ile Ser Ala Glu
            20                  25                  30

<210> SEQ ID NO 41
<211> LENGTH: 17
<212> TYPE: PRT
<213> ORGANISM: Artificial Sequence
<220> FEATURE:
<223> OTHER INFORMATION: recombinant genetic material from human/
      bacterial

<400> SEQUENCE: 41

Val Ile Asp Glu Val Arg His Leu Ala Ala Asn Gly Ile Lys Tyr Pro
```

```
1               5                   10                  15
Glu

<210> SEQ ID NO 42
<211> LENGTH: 16
<212> TYPE: PRT
<213> ORGANISM: Artificial Sequence
<220> FEATURE:
<223> OTHER INFORMATION: recombinant genetic material from human/
      bacterial

<400> SEQUENCE: 42

Met Gly Thr Val Tyr Ser Thr Leu Gly Ser Arg Leu Asp Val Val Glu
1               5                   10                  15

<210> SEQ ID NO 43
<211> LENGTH: 10
<212> TYPE: PRT
<213> ORGANISM: Artificial Sequence
<220> FEATURE:
<223> OTHER INFORMATION: recombinant genetic material from human/
      bacterial

<400> SEQUENCE: 43

Ile Ile Gly Gly Gly Ile Ile Gly Leu Glu
1               5                   10

<210> SEQ ID NO 44
<211> LENGTH: 15
<212> TYPE: PRT
<213> ORGANISM: Artificial Sequence
<220> FEATURE:
<223> OTHER INFORMATION: recombinant genetic material from human/
      bacterial

<400> SEQUENCE: 44

Met Asp Val Pro Ala Glu Val Ala Gly Val Val Lys Glu Val Lys
1               5                   10                  15

<210> SEQ ID NO 45
<211> LENGTH: 24
<212> TYPE: PRT
<213> ORGANISM: Artificial Sequence
<220> FEATURE:
<223> OTHER INFORMATION: recombinant genetic material from human/
      bacterial

<400> SEQUENCE: 45

Asn Ser Asp Ser Glu Cys Pro Leu Ser His Asp Gly Tyr Cys Leu His
1               5                   10                  15

Asp Gly Val Cys Met Tyr Ile Glu
            20

<210> SEQ ID NO 46
<211> LENGTH: 20
<212> TYPE: PRT
<213> ORGANISM: Artificial Sequence
<220> FEATURE:
<223> OTHER INFORMATION: recombinant genetic material from human/
      bacterial

<400> SEQUENCE: 46

Val Val Val Leu Gly Gly Gly Pro Gly Gly Tyr Ser Ala Ala Phe Ala
1               5                   10                  15

Ala Ala Asp Glu
            20
```

<210> SEQ ID NO 47
<211> LENGTH: 18
<212> TYPE: PRT
<213> ORGANISM: Artificial Sequence
<220> FEATURE:
<223> OTHER INFORMATION: recombinant genetic material from human/
      bacterial

<400> SEQUENCE: 47

Leu Lys Val Pro Asp Ile Gly Gly His Glu Asn Val Asp Ile Ile Ala
1               5                   10                  15

Val Glu

<210> SEQ ID NO 48
<211> LENGTH: 12
<212> TYPE: PRT
<213> ORGANISM: Artificial Sequence
<220> FEATURE:
<223> OTHER INFORMATION: recombinant genetic material from human/
      bacterial

<400> SEQUENCE: 48

Arg Cys Gln Tyr Arg Asp Leu Lys Trp Trp Glu Leu
1               5                   10

<210> SEQ ID NO 49
<211> LENGTH: 31
<212> TYPE: PRT
<213> ORGANISM: Artificial Sequence
<220> FEATURE:
<223> OTHER INFORMATION: recombinant genetic material from human/
      bacterial

<400> SEQUENCE: 49

Val Asp Lys Gln Met Arg Thr Asn Val Pro His Ile Tyr Ala Ile Gly
1               5                   10                  15

Asp Ile Val Gly Gln Pro Met Leu Ala His Lys Ala Val His Glu
            20                  25                  30

<210> SEQ ID NO 50
<211> LENGTH: 22
<212> TYPE: PRT
<213> ORGANISM: Artificial Sequence
<220> FEATURE:
<223> OTHER INFORMATION: recombinant genetic material from human/
      bacterial

<400> SEQUENCE: 50

Ala Ser Gly Arg Ala Ile Ala Asn Gly Cys Asp Asn Gly Phe Thr Lys
1               5                   10                  15

Leu Ile Phe Asp Ala Glu
            20

<210> SEQ ID NO 51
<211> LENGTH: 27
<212> TYPE: PRT
<213> ORGANISM: Artificial Sequence
<220> FEATURE:
<223> OTHER INFORMATION: recombinant genetic material from human/
      bacterial

<400> SEQUENCE: 51

Tyr Arg Phe Asp Asn Ile Met Val Asn Thr Lys Thr Val Ala Val Glu
1               5                   10                  15

```
Pro Lys Glu Asp Gly Val Tyr Val Thr Phe Glu
            20                  25
```

<210> SEQ ID NO 52
<211> LENGTH: 18
<212> TYPE: PRT
<213> ORGANISM: Artificial Sequence
<220> FEATURE:
<223> OTHER INFORMATION: recombinant genetic material from human/
      bacterial

<400> SEQUENCE: 52

```
Ala Ile Ala Asn Gly Cys Asp Asn Gly Phe Thr Lys Leu Ile Phe Asp
1               5                   10                  15

Ala Glu
```

<210> SEQ ID NO 53
<211> LENGTH: 29
<212> TYPE: PRT
<213> ORGANISM: Artificial Sequence
<220> FEATURE:
<223> OTHER INFORMATION: recombinant genetic material from human/
      bacterial

<400> SEQUENCE: 53

```
Arg Tyr Lys Thr Leu Gly Gly Val Cys Leu Asn Val Gly Cys Ile Pro
1               5                   10                  15

Ser Lys Ala Leu Leu His Asn Ala Ala Val Ile Asp Glu
            20                  25
```

<210> SEQ ID NO 54
<211> LENGTH: 17
<212> TYPE: PRT
<213> ORGANISM: Artificial Sequence
<220> FEATURE:
<223> OTHER INFORMATION: recombinant genetic material from human/
      bacterial

<400> SEQUENCE: 54

```
Val Asn Val Gly Asp Thr Ile Ala Val Asp Asp Thr Leu Ile Thr Leu
1               5                   10                  15

Asp
```

<210> SEQ ID NO 55
<211> LENGTH: 30
<212> TYPE: PRT
<213> ORGANISM: Artificial Sequence
<220> FEATURE:
<223> OTHER INFORMATION: recombinant genetic material from human/
      bacterial

<400> SEQUENCE: 55

```
Ile Val Gly Gln Pro Met Leu Ala His Lys Ala Val His Glu Gly His
1               5                   10                  15

Val Ala Ala Glu Asn Cys Ala Gly His Lys Ala Tyr Phe Asp
            20                  25                  30
```

<210> SEQ ID NO 56
<211> LENGTH: 31
<212> TYPE: PRT
<213> ORGANISM: Artificial Sequence
<220> FEATURE:
<223> OTHER INFORMATION: recombinant genetic material from human/
      bacterial

<400> SEQUENCE: 56

```
Asn Gly Phe Thr Lys Leu Ile Phe Asp Ala Glu Thr Gly Arg Ile Ile
1               5                   10                  15

Gly Gly Gly Ile Val Gly Pro Asn Gly Gly Asp Met Ile Gly Glu
                20                  25                  30

<210> SEQ ID NO 57
<211> LENGTH: 30
<212> TYPE: PRT
<213> ORGANISM: Artificial Sequence
<220> FEATURE:
<223> OTHER INFORMATION: recombinant genetic material from human/
      bacterial

<400> SEQUENCE: 57

Thr Gly Arg Ile Ile Gly Gly Gly Ile Val Gly Pro Asn Gly Gly Asp
1               5                   10                  15

Met Ile Gly Glu Val Cys Leu Ala Ile Glu Met Gly Cys Asp
                20                  25                  30
```